United States Patent
Boström et al.

(10) Patent No.: US 7,432,288 B2
(45) Date of Patent: Oct. 7, 2008

(54) PYRROLE-2,5-DIONE DERIVATIVES AS LIVER X RECEPTOR MODULATORS

(75) Inventors: Jonas Boström, Mölndal (SE); Kay Brickmann, Mölndal (SE); Patrik Holm, Pargas (FI); Pernilla Sandberg, Mölndal (SE); Marianne Swanson, Mölndal (SE); Christer Westerlund, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 1 day.

(21) Appl. No.: 10/564,235

(22) PCT Filed: Jul. 8, 2004

(86) PCT No.: PCT/SE2004/001114

§ 371 (c)(1),
(2), (4) Date: Jun. 6, 2006

(87) PCT Pub. No.: WO2005/005417

PCT Pub. Date: Jan. 20, 2005

(65) Prior Publication Data

US 2006/0235015 A1    Oct. 19, 2006

(30) Foreign Application Priority Data

Jul. 11, 2003  (GB)  .................... 0316232.8

(51) Int. Cl.
*A61K 31/4439*  (2006.01)
*C07D 401/04*   (2006.01)

(52) U.S. Cl. .................... 514/343; 546/278.7
(58) Field of Classification Search ........... 546/278.7; 514/343
See application file for complete search history.

(56) References Cited

FOREIGN PATENT DOCUMENTS

| WO | WO 00/06564 | 2/2000 |
|----|-------------|--------|
| WO | WO-00/21927 | 4/2000 |
| WO | WO-01/03705 | 1/2001 |
| WO | WO 01/13916 | 3/2001 |
| WO | WO 01/74771 | 10/2001 |

OTHER PUBLICATIONS

Vippagunta et all., "Crystalline solids", Advanced Drug Delivery Reviews, 48 (2001), 3-26.*
Guillory "Generation of polymorphs, etc.," in Brittain ed., Polymorphism in Pharmaceutical Solids, 95, Marcel Dekker, NY, 1999, 183-226.*
Laffitte et al. "Activation of liver X receptor improves glucose tolerance through coordinate regulation of glucose metabolism in liver and adipose tissue" PNAS 100: 5419-5424 (2003).

* cited by examiner

*Primary Examiner*—Patricia L Morris
(74) *Attorney, Agent, or Firm*—Morgan, Lewis & Bockius LLP

(57) ABSTRACT

The present invention relates to certain novel compounds of the Formula I

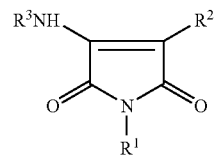

Formula I to processes for preparing such compounds, to their the utility in modulation of nuclear hormone receptors Liver X Receptor (LXR)α(NR1H3) and/or β(NR1H2) and in treating and/or preventing clinical conditions including cardiovascular diseases such as atherosclerosis; inflammatory diseases, Alzheimer's disease, lipid disorders (dyslipidemias) whether or not associated with insulin resistance, type 2 diabetes and other manifestations of the metabolic syndrome, to methods for their therapeutic use and to pharmaceutical compositions containing them.

12 Claims, No Drawings

PYRROLE-2,5-DIONE DERIVATIVES AS LIVER X RECEPTOR MODULATORS

RELATED APPLICATIONS

This application is a national stage filing under 35 U.S.C. 371 of International Application PCT/SE2004/001114, filed Jul. 8, 2004, which claims the benefit of Great Britain Application No. 0316232.8, filed Jul. 11, 2003, the specifications of each of which are incorporated by reference herein. International Application PCT/SE2004/001114 was published under PCT Article 21(2) in English.

FIELD OF THE INVENTION

The present invention relates to certain novel 1-(substituted alkyl)-3amino-4phenyl-1H-pyrrole-2,5-dione derivatives, to processes for preparing such compounds, to their the utility in modulation of nuclear hormone receptors Liver X Receptor (LXR) α (NR1H3) and/or β (NR1H2) and in treating and/or preventing clinical conditions including cardiovascular diseases such as atherosclerosis; inflammatory diseases, Alzheimer's disease, lipid disorders (dyslipidemias) whether or not associated with insulin resistance, type 2 diabetes and other manifestations of the metabolic syndrome, to methods for their therapeutic use and to pharmaceutical compositions containing them.

BACKGROUND OF THE INVENTION

Abnormalities of cholesterol and fatty acid homeostasis, that are reflected as diverse dyslipidemias, are causal of atherosclerosis and consequently cardiovascular disease (CVD). This disease is one of the major health problems in industrialized countries and is reaching the same prevalence in adults in developing nations. Most studies show that statins reduce low density lipoproteins (LDL) cholesterol by 25-30% and the relative risk of coronary events by approximately 30%. While this beneficial effect is significant, effectively 70% of the treated cohort remains with unchanged risk. This has prompted intense research in order to identify other common abnormalities of lipid metabolism that if efficiently treated could improve the results of current CVD therapy.

The nuclear hormone receptors LXR α and β use oxysterols as natural ligands. They appear to act as cholesterol sensors with target genes that are required for cholesterol efflux from macrophages, like ATP binding casette transporter A1 (ABCA1) and apoE, as well as gene products, like cholesterol ester transferase protein (CETP) and phospholipid transport protein (PLTP), that are required for the function of high density lipoprotein (HDL) in the reverse cholesterol transport. In addition, LXR upregulates lipoprotein lipase in liver and macrophages, a function that may stimulate fatty acid uptake and very low density lipoprotein (VLDL) remodeling. In the liver, LXR ligands seem to stimulate the hepatobiliary secretion of cholesterol, a pathway controlled by the ABCG5 and ABCG8. The same cholesterol transporters appear to reduce cholesterol absorption in enterocytes, therefore influencing total body cholesterol balance. These effects of LXR stimulation could explain its remarkable anti-atherosclerotic properties observed in animal models.

Recently the synthetic LXR ligands GW3965 (Glaxo) and T-0901317 (Tularik) were reported to increase glucose tolerance in fat fed obese mouse, which was interpreted to result from reduced hepatic gluconeogenesis and increased glucose uptake in adipocytes Lafitte BA et al. (Proc Natl Acad Sci USA. 2003 Apr. 29;100(9):5419-24). Activation of LXR's improves glucose tolerance through coordinated regulation of glucose metabolism in liver and adipose tissue.

WO00/21927 discloses pyrrole-2,5-diones, which are GSK-3 inhibitors and claimed to be useful in the treatment of dementias such as Alzheimer's disease, manic depression and diabetes. There is no suggestion that these compounds have activity as LXR modulators.

The term "LXR modulator" as used herein, means a small molecule that modulates the biological activities of LXRα and/or LXRβ. More specifically, such an LXR modulator either enhances or inhibits the biological activities of LXR. If such a modulator partially or completely enhances the biological activities of LXR, it is a partial or full LXR agonist, respectively. It is the object of the present invention to provide LXR modulators. Another object of this invention is to provide LXR modulator compounds being LXR agonists.

DESCRIPTION OF THE INVENTION

According to a first aspect of the present invention there is provided a compound of formula I:

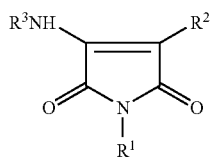

Formula I wherein:
$R^1$ is selected from phenyl(1-4C)alkyl wherein the phenyl is substituted by (1-4C)alkoxycarbonyl or a group of formula $NR^aR^b$ in which $R^a$ and $R^b$ independently represent H or (1-4C)alkyl; heteroaryl(1-4C)alkyl wherein the heteroaryl optionally is substituted by (1-4C)alkyl or a group of formula $NR^aR^b$ in which $R^a$ and $R^b$ independently represent H or (1-4C)alkyl; or a (1-4C)alkyl group which is substituted by one or more of the following: fluoro, (1-4C)alkoxycarbonyl, (1-3C)alkylthio or (1-3C)alkoxy optionally substituted by one or more fluoro;

$R^2$ is phenyl;

$R^3$ is selected from phenyl, indolyl or benzofuranyl each optionally substituted by one or more of the following: (1-3C) alkanoyl, (1-3C)alkoxy optionally substituted by one or more fluoro; (1-3C)alkylthio; or a group of formula $NR^aR^b$ in which $R^a$ and $R^b$ independently represent H, (1-3C)alkyl or (1-3C)alkanoyl or $R^a$ and $R^b$ together with the nitrogen atom to which they are attached represent morpholino, or a pharmaceutically acceptable salt or solvate thereof, or a solvate of such a salt.

The term heteroaryl means pyridyl, furyl or isoxazolyl each of which is optionally substituted by one or more of the following: (1-4C)alkyl or a group of formula $NR^aR^b$ in which $R^a$ and $R^b$ independently represent H or (1-4C)alkyl.

Further values of $R^1$, $R^2$ and $R^3$ in compounds of formula I now follow. It will be understood that such values may be used where appropriate with any of the definitions, claims or embodiments defined hereinbefore or hereinafter.

$R^1$ is selected from 2-methoxyethyl, 2-methylthioethyl, 2,2,2-trifluoroethyl, 3-methoxypropyl, 3,3,3-trifluoropropyl, ethoxycarbonylmethyl, 4-N,N-dimethylaminobenzyl, 4-methoxycarbonylbenzyl, 2-pyridylmethyl, 3-pyridylmethyl, 4-pyridylmethyl, 6-amino-3-pyridylmethyl, 3-furylmethyl or (5-methylisoxazol-3yl)methyl.

R³ is selected from phenyl, 4-methoxyphenyl, 4-methylthiophenyl, 4-morpholinophenyl, 4-acetylaminophenyl, 4-trifluoromethoxyphenyl, 4-difluoromethoxyphenyl or 2-acetyl-5-benzofuranyl.

In a first group of compounds of formula I
R¹ is selected from 2-methoxyethyl, 2,2,2-trifluoroethyl, 3,3,3-trifluoropropyl, 3-methoxypropyl, ethoxycarbonylmethyl, 2-pyridylmethyl, 3-pyridylmethyl, 4-pyridylmethyl, 6-amino-3-pyridylmethyl or (5-methylisoxazol-3yl)methyl;
R² is phenyl;
R³ is selected from phenyl, 4-methoxyphenyl, 4-acetylaminophenyl, 4-difluoromethoxyphenyl or 4-morpholinophenyl.

In a second group of compounds of formula I
R¹ is selected from 2-methoxyethyl, 6-amino-3-pyridylmethyl, 3-pyridylmethyl or 2,2,2-trifluoroethyl;
R² is phenyl; and
R³ is selected from 4-methoxyphenyl, 4-difluoromethoxyphenyl, 4-trifluoromethoxyphenyl or 4-morpholinophenyl.

In a third group of compounds of formula I
R¹ is selected from 2,2,2-trifluoroethyl, 3-furylmethyl, 6-amino-3-pyridylmethyl or 3-pyridylmethyl;
R² is phenyl; and
R³ is selected from 4-methoxyphenyl, 4-difluoromethoxyphenyl, 4-morpholinophenyl or 2-acetyl-5-benzofuranyl.

In a fourth group of compounds of formula I
R¹ is selected from 6-amino-3-pyridylmethyl or 2-methoxyethyl;
R² is phenyl; and
R³ is selected from 4-morpholinophenyl, 4-trifluoromethoxyphenyl or 4-difluoromethoxyphenyl.

In a fifth group of compounds of formula I
R¹ is selected from 6-amino-3-pyridylmethyl, 3-furylmethyl, 3-pyridylmethyl, 2,2,2-trifluoroethyl or 2-methoxyethyl;
R² is phenyl; and
R³ is selected from 4-morpholinophenyl, 4-methoxyphenyl, 4-trifluoromethoxyphenyl, 4-difluoromethoxyphenyl or 2-acetyl-5-benzofuranyl.

The compounds of formula I have activity as medicaments. In particular the compounds of formula I are LXR agonists.

Specific compounds of the invention are one or more of the following:

1-(2-Methoxyethyl)-3-[(4-methoxyphenyl)amino]-4-phenyl-1H-pyrrole-2,5-dione 3-{[4-(Difluoromethoxy)phenyl]amino}-1-(2-methoxyethyl)-4-phenyl-1H-pyrrole-2,5-dione
N-(4-{[2,5-Dihydro-1-(2-methoxyethyl)-2,5-dioxo-4-phenyl-1H-pyrrol-3-yl]amino}phenyl)-acetamide
1-(2-Methoxyethyl)-3-{[4(methylthio)phenyl]amino}-4-phenyl-1H-pyrrole-2,5-dione
3-[(2-Acetyl-5-benzofuranyl)amino]-1-(2-methoxyethyl)-4-phenyl-1H-pyrrole-2,5-dione
1-(2-Methoxyethyl)-3-[(4-morpholin-4-ylphenyl)amino]-4-phenyl-1H-pyrrole-2,5-dione
3-[(4-Morpholin-4-ylphenyl)amino]-4-phenyl-1-(pyridin-3-ylmethyl)-1H-pyrrole-2,5-dione
3-[(2-Acetyl-5-benzofuranyl)amino]-4-phenyl-1-(pyridin-3-ylmethyl)-1H-pyrrole-2,5-dione
3-Phenyl-1-(pyridin-3-ylmethyl)-4-{[4-(trifluoromethoxy)phenyl]amino}-1H-pyrrole-2,5-dione
3-[(4-Methoxyphenyl)amino]-4-phenyl-1-(pyridin-3-ylmethyl)-1H-pyrrole-2,5-dione
3-Anilino-4-phenyl-1-(pyridin-3-ylmethyl)-1H-pyrrole-2,5-dione
3-{[4-(Difluoromethoxy)phenyl]amino}-4-phenyl-1-(pyridin-3-ylmethyl)-1H-pyrrole-2,5-dione
1-[4-(Dimethylamino)benzyl]-3-[(4-methoxyphenyl)amino]-4-phenyl-1H-pyrrole-2,5-dione
3-[(4-Methoxyphenyl)amino]-4-phenyl-1-(pyridin-4-ylmethyl)-1H-pyrrole-2,5-dione
3-[(4-Methoxyphenyl)amino]-4-phenyl-1-(pyridin-2-ylmethyl)-1H-pyrrole-2,5-dione
3-[(4-Methoxyphenyl)amino]-1-(3-methoxypropyl)-4-phenyl-1H-pyrrole-2,5-dione
Methyl 4-({3-[(4-methoxyphenyl)amino]-2,5-dioxo-4-phenyl-2,5-dihydro-1H-pyrrol-1-yl}methyl)benzoate
3-[(4-Methoxyphenyl)amino]-1-[2-(methylthio)ethyl]-4-phenyl-1H-pyrrole-2,5-dione
3-[(4-Methoxyphenyl)amino]-4-phenyl-1-(3,3,3-trifluoropropyl)-1H-pyrrole-2,5-dione
1-(3-Furylmethyl)-3-[(4-methoxyphenyl)amino]-4-phenyl-1H-pyrrole-2,5-dione
3-[(4-Methoxyphenyl)amino]-4-phenyl-1-(2,2,2-trifluoroethyl)-1H-pyrrole-2,5-dione
3-[(4-Methoxyphenyl)amino]-1-[(5-methylisoxazol-3-yl)methyl]-4-phenyl-1H-pyrrole-2,5-dione
Ethyl {3-[(4-methoxyphenyl)amino]-2,5-dioxo-4-phenyl-2,5-dihydro-1H-pyrrol-1-yl}acetate
3-Phenyl-1-(2,2,2-trifluoroethyl)-4-{[4-(trifluoromethoxy)phenyl]amino}-1H-pyrrole-2,5-dione
1-[(6-Aminopyridin-3-yl)methyl]-3-[(4-methoxyphenyl)amino]-4-phenyl-1H-pyrrole-2,5-dione
1-[(6-Aminopyridin-3-yl)methyl]-3-{[4-(difluoromethoxy)phenyl]amino}-4-phenyl-1H-pyrrole-2,5-dione and
1-[(6-Aminopyridine-3-yl)methyl]-3-[(4-morpholin-4-ylphenyl)amino]-4-phenyl-1-H-pyrrole-2,5-dione, or a pharmaceutically acceptable salt or solvate thereof, or a solvate of such a salt.

Certain compounds of the present invention may exist as tautomers. It is to be understood that the present invention encompasses all such tautomers.

Methods of Preparation

The compounds of the invention may be prepared as outlined below. However, the invention is not limited to these methods. The compounds may also be prepared as described for structurally related compounds in the prior art. The reactions can be carried out according to standard procedures or as described in the experimental section.

Compounds of formula I may be prepared by reacting a compound of formula II

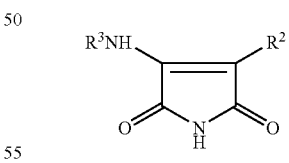

in which R² and R³ are as previously defined with a compound of formula III

R¹OH    III in which R¹ is as previously defined in the presence of a dialkyl azodicarboxylate, for example diethyl azodicarboxylate, and a phosphine, for example triphenylphosphine, optionally in the presence of an inert organic liquid for example an ether e.g. tetrahydrofuran at a temperature in the range of 0° C. to 200° C.

Compounds of formula I may also be prepared by reacting a compound of formula IV

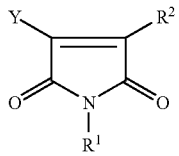

IV in which $R^1$ and $R^2$ are as previously defined and Y is a leaving group for example halo e.g. Cl, Br or I with a compound of formula V $R^3NH_2$    V in which $R^3$ is as previously defined optionally in the presence of an inert organic liquid for example dimethylformamide optionally in the presence of a base for example potassium carbonate at a temperature in the range of 0° C. to 250° C.

Compounds of formula II may be prepared by reacting a compound of formula VI

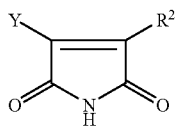

VI in which R2 is as previously defined and Y is a leaving group for example halo eg Cl, Br or I with a compound of formula V $R^3NH_2$    V in which $R^3$ is as previously defined optionally in the presence of an inert organic liquid for is example dimethylformamide and optionally in the presence of a base for example triethylamine at a temperature in the range of 0° C. to 250° C.

Compounds of formula III and V are commercially available or may be prepared by methods known to those skilled in the art.

Compounds of formula IV may be prepared by reacting a compound of formula VII

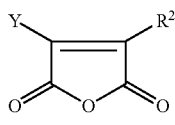

VII in which $R^2$ is as previously defined and Y is a leaving group for example halo eg Cl, Br or I with a compound of formula VIII $R^1NH_2$    VIII in which $R^1$ is as previously defined optionally in the presence of an organic liquid, for example glacial acetic acid at a temperature in the range of 0° C. to 200° C.

Compounds of formula IV may also be prepared by reacting a compound of formula VI with a compound of formula XI $R^1L$    XI in which $R^1$ is as as previously defined and L is a leaving group for example halo eg Cl, Br or I in the presence of an inert organic liquid for example dimethylformamide and optionally in the presence of a base for example potassium carbonate at a temperature in the range of −78° C. to 200° C.

Compounds of formula VI may be prepared by reacting a compound of formula IX

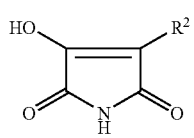

IX in which $R^2$ is as previously defined with a halogenating agent for example oxalyl chloride optionally in the presence of an inert organic liquid for example dichloromethane and optionally in the presence of a catalytic amount of dimethylformamide at a temperature in the range of 0° C. to 200° C.

Compounds of formula VII may be prepared by reacting a compound of formula X

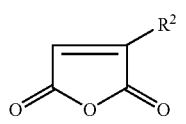

X in which $R^2$ is as previously defined with a halogenating agent for example thionyl chloride optionally in the presence of an inert organic liquid for example dichloromethane and optionally in the presence of a base for example pyridine at a temperature in the range of 0° C. to 200° C.

Compounds of formula VIII, IX, X and XI are commercially available or may be prepared by methods known to those skilled in the art.

Certain compounds of formula II and IV are believed to be novel and are claimed herein as useful intermediates in the preparation of compounds of formula I.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

The expression "inert organic liquid" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001-100 mg/kg body weight, preferably 0.01-10 mg/kg body weight.

Oral formulations are preferred particularly tablets or capsules which may be formulated by methods known to those skilled in the art to provide doses of the active compound in the range of 0.7 mg to 700 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The compounds of formula I are useful for normalization of cholesterol homeostasis, decreasing intestinal cholesterol absorption, improving reverse cholesterol transport, improving HDL functionality, increasing HDL-cholesterol levels, decreasing LDL-cholesterol levels, decreasing cholesterol content of apoB-containing lipoproteins, stimulating cholesterol efflux from vascular cells and/or decreasing the inflammatory response of vascular cells. As a consequence of these properties the compounds of formula I are expected to have anti-atherosclerotic effects.

The compounds of formula I are useful in the prevention or treatment of cardiovascular disease in a mammal, particularly a human. The compounds of formula I are useful in the prevention or treatment of atherosclerosis in a mammal, particularly a human. Cardiovascular disease includes but is not limited to conditions associated with atherosclerosis, arteriosclerosis, hypercholesterolemia, and other kinds of dyslipidemia that increase the risk for cardiovascular disease. In particular the compounds of formula I are useful in the treatment or prevention of cardiovascular disease, especially those involving atherosclerosis and hypercholesterolemia.

The compounds of formula I also serve to prevent lipid accumulation in, or remove lipids from, tissue deposits such as atherosclerotic plaques or xanthomas in a patient with atherosclerotic disease manifest by clinical signs such as angina, claudication, bruits, one that has suffered a mycardial infarction or transient ischemic attack, or one diagnosed by angiography, sonography or MRI.

The compounds of formula I also serve to prevent or reduce the risk of developing atherosclerosis, as well as for halting or slowing the progression of atherosclerotic disease once it has become clinically evident, comprising the administration of a prophylactically or therapeutically effective amount, as appropriate, of a compound of formula I to a mammal, including a human, who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease".

The present compounds of formula I are also useful for the prophylaxis and/or treatment of clinical conditions associated with atherosclerosis such as inherent or induced hypercholesterolemia as well as inherent or induced reduced sensitivity to insulin (insulin resistance syndrome also known as metabolic syndrome) and associated metabolic disorders. These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated VLDL triglyceride rich particles, high ApoB levels, low HDL levels associated with low apoAI levels in the presence of small, dense, LDL particles, phenotype B.

The compounds of formula I are expected to be useful in treating patients with combined or mixed hyperlipidemias and dyslipidemias, especially low HDL levels with or without other manifestations of the metabolic syndrome.

Treatment with the compounds of formula I are expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. The insulin sensitizing effect of the compounds of formula I is also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed.

The compounds of formula I may also be useful for the prevention or treatment of inflammation and neurodegenerative diseases or neurological disorders. Accordingly, this invention also provides a method for preventing or treating inflammation in the CNS and a method for preventing or treating neurodegenerative diseases or disorders characterized by neuron degeneration, neuron injury or impaired plasticity or inflammation in the CNS. The neurodegenerative diseases or conditions characterized by neuron degeneration and inflammation will include but will not be limited to stroke, Alzheimer's disease, fronto-temporal dementias (taupathies), peripheral neuropathy, Parkinson's disease, dementia with Lewy bodies, Huntington's disease, amyotrophic lateral sclerosis and multiple sclerosis.

The compounds of formula I are useful in preventing or treating inflammatory conditions or diseases. These diseases or conditions will include but will not be limited to atherosclerotic diseases such as angina pectoris and myocardial infarction as well as inflammatory bowel diseases or conditions such as Crohn's disease, ulcerative colitis and distal proctitis. Compounds of formula I may also be used in other inflammatory conditions of the lung including asthma, adult respiratory distress syndrome, chronic obstructive pulmonary disease and pneumonia bronchitis.

Furthermore the compounds of formula I may be useful in treatment of various conditions outside the cardiovascular system whether or not associated with insulin resistance, like polycystic ovarian syndrome, obesity and cancer.

The present invention provides a method of treating and/or preventing dyslipidemias, the insulin resistance syndrome and/or metabolic disorders (as defined above) comprising the administration of a compound of formula I to a mammal (particularly a human) in need thereof.

The present invention provides a method of treating and/or preventing type 2 diabetes comprising the administration of an effective amount of a compound of formula I to a mammal (particularly a human) in need thereof.

The present invention provides a method of treating and/or preventing cardiovascular disease comprising the administration of an effective amount of a compound of formula I to a mammal (particularly a human) in need thereof.

The present invention provides a method of treating and/or preventing atherosclerosis comprising the administration of an effective amount of a compound of formula I to a mammal (particularly a human) in need thereof.

The present invention provides a method of treating and/or preventing hypercholesterolemia comprising the administration of an effective amount of a compound of formula I to a mammal (particularly a human) in need thereof.

The present invention provides a method of treating and/or preventing conditions associated with a need for improving reverse cholesterol transport comprising the administration of an effective amount of a compound of formula I to a mammal (particularly a human) in need thereof.

The present invention provides a method of treating and/or preventing conditions associated with a need for decreasing intestinal cholesterol absorption comprising the administration of an effective amount of a compound of formula I to a mammal (particularly a human) in need thereof.

The present invention provides a method of treating and/or preventing conditions associated with a need for increasing HDL-cholesterol levels comprising the administration of an effective amount of a compound of formula I to a mammal (particularly a human) in need thereof.

The present invention provides a method of treating and/or preventing conditions associated with a need for decreasing LDL-cholesterol levels comprising the administration of an effective amount of a compound of formula I to a mammal (particularly a human) in need thereof.

The present invention provides a method of treating and/or preventing inflammatory conditions comprising the administration of an effective amount of a compound of formula I to a mammal (particularly a human) in need thereof.

The present invention provides a method of treating and/or preventing Alzheimer's disease comprising the administration of an effective amount of a compound of formula I to a mammal (particularly a human) in need thereof.

The present invention provides a method of treating and/or preventing arteriosclerosis comprising the administration of an effective amount of a compound of formula I to a mammal (particularly a human) in need thereof.

The present invention provides a method of treating and/or preventing conditions associated with a need for improving HDL function comprising the administration of an effective amount of a compound of formula I to a mammal (particularly a human) in need thereof.

The present invention provides a method of treating and/or preventing hyperlipidemic conditions comprising the administration of an effective amount of a compound of formula I to a mammal (particularly a human) in need thereof.

In a further aspect the present invention provides the use of a compound of formula I as a medicament.

In a further aspect the present invention provides the use of a compound of formula I in the manufacture of a medicament for the treatment and/or prohylaxis of dyslipidemic conditions.

In a further aspect the present invention provides the use of a compound of formula I in the manufacture of a medicament for the treatment and/or prohylaxis of insulin resistance and/or metabolic disorders.

In a further aspect the present invention provides the use of a compound of formula I in the manufacture of a medicament for the treatment and/or prophylaxis of cardiovascular disease.

In a further aspect the present invention provides the use of a compound of formula I in the manufacture of a medicament for the treatment and/or prophylaxis of atherosclerosis.

In a further aspect the present invention provides the use of a compound of formula I in the manufacture of a medicament for the treatment and/or prophylaxis of hypercholesterolemia.

In a further aspect the present invention provides the use of a compound of formula I in the manufacture of a medicament for the treatment and/or prophylaxis of conditions associated with a need for improving reverse cholesterol transport.

In a further aspect the present invention provides the use of a compound of formula I in the manufacture of a medicament for the treatment and/or prophylaxis of conditions associated with a need for decreasing intestinal cholesterol absorption.

In a further aspect the present invention provides the use of a compound of formula I in the manufacture of a medicament for the treatment and/or prophylaxis of conditions associated with a need for increasing HDL-cholesterol levels.

In a further aspect the present invention provides the use of a compound of formula I in the manufacture of a medicament for the treatment and/or prophylaxis of conditions associated with a need for decreasing LDL-cholesterol levels.

In a further aspect the present invention provides the use of a compound of formula I in the manufacture of a medicament for the treatment and/or prophylaxis of inflammatory conditions.

In a further aspect the present invention provides the use of a compound of formula I in the manufacture of a medicament for the treatment and/or prophylaxis of Alzheimer's disease.

In a further aspect the present invention provides the use of a compound of formula I in the manufacture of a medicament for the treatment and/or prophylaxis of arteriosclerosis.

In a further aspect the present invention provides the use of a compound of formula I in the manufacture of a medicament for the treatment and/or prophylaxis of type 2 diabetes.

In a further aspect the present invention provides the use of a compound of formula I in the manufacture of a medicament for the treatment and/or prophylaxis of conditions associated with a need for improving HDL function.

In a further aspect the present invention provides the use of a compound of formula I in the manufacture of a medicament for the treatment and/or prophylaxis of hyperlipidemic conditions.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes, inflammation and obesity. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

In another aspect of the present invention, the compound of formula I, or a pharmaceutically acceptable salt or solvate thereof, or a solvate of such a salt, may be administered in association with cholesterol biosynthesis inhibitors, or pharmaceutically acceptable salts, solvates, solvates of such salts or prodrugs thereof. Suitable cholesterol biosynthesis inhibitors include HMG CoA reductase inhibitors, squalene synthesis inhibitors and squalene epoxidase inhibitors. A suitable squalene synthesis inhibitor is squalestatin 1 and a suitable squalene epoxidase inhibitor is NB-598.

In this aspect of the invention, the compound of formula I, or a pharmaceutically acceptable salt or solvate thereof, or a solvate of such a salt, may be administrated in association with an HMG CoA reductase inhibitor, or pharmaceutically acceptable salts, solvates, solvates of such salts or prodrugs thereof. Suitably the HMG CoA reductase inhibitor, or pharmaceutically acceptable salts, solvates, solvates of such salts or prodrugs thereof are statins well known in the art. Particular statins are selected from the group consisting of atorvastatin, fluvastatin, pitavastatin, lovastatin, mevastatin, nicostatin, nivastatin, pravastatin and simvastatin, or a pharmaceutically acceptable salt, especially sodium or calcium, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A particularly preferred statin is, however, rosuvastatin, or a pharmaceutically acceptable salt, solvate, solvate of such a salt or a prodrug thereof. A preferable particular statin is rosuvastatin calcium salt.

In the present application, the term "cholesterol biosynthesis inhibitors" also includes chemical modifications of the HMG CoA reductase inhibitors, squalene synthesis inhibitors and squalene epoxidase inhibitors, such as esters, prodrugs and metabolites, whether active or inactive.

In another aspect of the present invention, the compound of formula I, or a pharmaceutically acceptable salt or solvate thereof, or a solvate of such a salt, may be administered in association with an inhibitor of the ileal bile acid transport system (IBAT inhibitor), or pharmaceutically acceptable salts, solvates, solvates of such salts or prodrugs thereof. Suitable compounds possessing IBAT inhibitory activity have been described, see for instance the compounds described in WO 93/16055, WO 94/18183, WO 94/18184, WO 96/05188, WO 96/08484, WO 96/16051, WO 97/33882, WO 98/07449, WO 98/03818, WO 98/38182, WO 99/32478, WO 99/35135, WO 98/40375, WO 99/35153, WO 99/64409, WO 99/64410, WO 00/01687, WO 00/47568, WO 00/61568, WO 00/62810, WO 01/68906, DE 19825804, WO 00/38725, WO 00/38726, WO 00/38727, WO 00/38728, WO 00/38729, WO 01/68906, WO 01/66533, WO 02/32428, WO 02/50051, EP 864 582, EP 489 423, EP 549 967, EP 573 848, EP 624 593, EP 624 594, EP 624 595 and EP 624 596 and the contents of these patent applications are incorporated herein by reference.

Further suitable compounds possessing IBAT inhibitory activity have been described in WO 94/24087, WO 98/56757, WO 00/20392, WO 00/20393, WO 00/20410, WO 00/20437, WO 01/34570, WO 00/35889, WO 01/68637, WO 02/08211, WO 03/020710, WO 03/022825, WO 03/022830, WO 03/022286, WO 03/091232, WO 03/106482, JP 10072371, U.S. Pat. No. 5,070,103, EP 251 315, EP 417 725, EP 869 121, EP 1 070 703 and EP 597 107 and the contents of these patent applications are incorporated herein by reference. Particular classes of IBAT inhibitors suitable for use in the present invention are benzothiazepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). A further suitable compound possessing IBAT inhibitory activity is S-8921 (EP 597 107).

In another aspect of the present invention, the compound of formula I, or a pharmaceutically acceptable salt or solvate thereof, or a solvate of such a salt, may be administered in association with a cholesterol absorption antagonist, or pharmaceutically acceptable salts, solvates, solvates of such salts or prodrugs thereof, for example azetidinones such as ezetrol (zetia, ezetimibe) and those described in U.S. Pat. No. 5,767,115 which are incorporated herein by reference. Suitable compounds possessing cholesterol absorption antagonist activity have been described, see for instance the compounds described in WO 02/50027, WO 02/66464, WO 04/005247, WO 04/000803, WO 04/000804 and WO 04/000805 which are incorporated herein by reference.

In another aspect of the present invention, the compound of formula I, or a pharmaceutically acceptable salt or solvate thereof, or a solvate of such a salt, may be administered in association with a bile acid sequestrant or pharmaceutically acceptable salts, solvates, solvates of such salts or prodrugs thereof. Suitable bile acid sequestrants include cholestyramine, cholestipol and cosevelam hydrochloride.

In another aspect of the invention, the compound of formula I, or a pharmaceutically acceptable salt or solvate thereof, or a solvate of such a salt, may be administered in association with a peroxisome proliferator-activated receptor (PPAR) modulating agent. PPAR modulating agents include but are not limited to a PPAR alpha and/or gamma and/or delta agonist, or pharmaceutically acceptable salts, solvates, solvates of such salts or prodrugs thereof. Suitable PPAR alpha and/or gamma and/or delta agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO 04/000790, WO 04/000295, WO 04/000294, WO 03/051822, WO 03/051821, WO 02/096863, WO 03/051826, WO 02/085844, WO 01/40172, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma and/or delta agonist refers to muraglitazar (BMS 298585), rivoglitazone (CS-011), netoglitazone (MCC-555), balaglitazone (DRF-2593, NN-2344), clofibrate, fenofibrate, bezafibrate, gemfibrozil, ciprofibrate, pioglitazone, rosiglitazone, AVE-0847, AVE-8134, CLX-0921, DRF-10945, DRF-4832, LY-518674, LY-818, LY-929, 641597, GW-590735, GW-677954, GW-501516, MBX-102, ONO-5129, KRP-101, R-483 (BM131258), TAK-559 or TAK-654. Particularly a PPAR alpha and/or gamma and/or delta agonist refers to tesaglitazar ((S)-2-ethoxy-3-[4-(2-{4-methanesulphonyl-oxyphenyl}ethoxy)phenyl]propanoic acid) and pharmaceutically acceptable salts thereof. In yet another aspect of the invention, the compound of formula I, or a pharmaceutically acceptable salt or solvate thereof, or a solvate of such a salt, may be administered in association with a pyruvate dehydrogenase kinase (PDK) inhibitor, or a pharmaceutically acceptable salt, solvate, solvate of such a salt or a prodrug thereof, or modulators of nuclear receptors such as retenoid X receptor (RXR), or a pharmaceutically acceptable salt, solvate, solvate of such a salt or a prodrug thereof.

In another aspect of the invention, the compound of formula I, or a pharmaceutically acceptable salt or solvate thereof, or a solvate of such a salt, may be administered in association with a cholesteryl ester transfer protein (CETP) inhibitor, or pharmaceutically acceptable salts, solvates, solvates of such salts or prodrugs thereof, for example those referenced and described in WO 00/38725 page 7 line 22—page 10, line 17 which are incorporated herein by reference.

In another aspect of the invention, the compound of formula I, or a pharmaceutically acceptable salt or solvate thereof, or a solvate of such a salt, may be administered in association with a microsomal transfer protein (MTP) inhibitor, or pharmaceutically acceptable salts, solvates, solvates of such salts or prodrugs thereof, for example implipatide and those described in WO 03/004020, WO 03/002533, WO 02/083658 and WO 00/242291, and the contents of these patent applications are incorporated herein by reference, or those described in Science, 282, 751-54, 1998 which are incorporated herein by reference.

In another aspect of the invention, the compound of formula I, or a pharmaceutically acceptable salt or solvate thereof, or a solvate of such a salt, may be administered in association with a nicotinic acid derivative, or pharmaceutically acceptable salts, solvates, solvates of such salts or prodrugs thereof, including slow release and combination products, for example, nicotinic acid (niacin), acipimox, nicofuranose, NIASPAN® and niceritrol.

In another aspect of the invention, the compound of formula I, or a pharmaceutically acceptable salt or solvate thereof, or a solvate of such a salt, may be administered in association with a acyl coenzymA: cholesterol O-acyltransferase (ACAT) inhibitor, or pharmaceutically acceptable salts, solvates, solvates of such salts or prodrugs thereof, for example CS-505, eflucimibe (F-12511) and SMP-797.

In yet another aspect of the invention, the compound of formula I, association with modulators of nuclear receptors such as farnesoid or a pharmaceutically acceptable salt or solvate thereof, or a solvate of such a salt, may be administered in X receptor (FXR), or pharmaceutically acceptable salt, solvate, solvate of such a salt or a prodrug thereof. In another aspect of the invention, the compound of formula I, or a pharmaceutically acceptable salt or solvate thereof, or a solvate of such a salt, may be administered in association with a phytosterol compound, or pharmaceutically acceptable salts, solvates, solvates of such salts or prodrugs thereof, for example stanols.

In another aspect of the invention, the compound of formula I, or a pharmaceutically acceptable salt or solvate thereof, or a solvate of such a salt, may be administered in association with other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt or solvate thereof, or a solvate of such a salt, may be administered in association with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

In another aspect of the invention, the compound of formula I, or a pharmaceutically acceptable salt or solvate thereof, or a solvate of such a salt, may be administered in association with an antihypertensive compound for example an angiotensin converting enzyme (ACE) inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, an AT-1 blocker, a saluretic, a diuretic or a vasodilator, or pharmaceutically acceptable salts, solvates, solvates of such salts or prodrugs thereof. Particular ACE inhibitors or pharmaceutically acceptable salts, solvates, solvate of such salts or prodrugs thereof, including active metabolites, which can be used in combination with a compound of formula I include but are not limited to, the following compounds: alacepril, alatriopril, ancovenin, benazepril, benazepril hydrochloride, benazeprilat, benzoyl-captopril, captopril, captopril-cysteine, captopril-glutathione, ceranopril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, hemorphin-4, imidapril, indolapril, indolaprilat, lisinopril, lyciumin A, lyciumin B, moexipril, moexiprilat, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat. Preferred angiotensin II receptor antagonists, pharmaceutically acceptable salts, solvates, solvate of such salts or a prodrugs thereof for use in combination with a compound of formula I include, but are not limited to, compounds: candesartan, candesartan cilexetil, losartan, valsartan, irbesartan, telmisartan and eprosartan. Particularly preferred angiotensin II receptor antagonists or pharmaceutically acceptable derivatives thereof for use in the present invention are candesartan and candesartan cilexetil.

In another aspect of the invention, the compound of formula I, or a pharmaceutically acceptable salt or solvate thereof, or a solvate of such a salt, may be administered in association with an anti-obesity compound, or pharmaceutically acceptable salts, solvates, solvates of such salts or prodrugs thereof, for example a pancreatic lipase inhibitor e.g. orlistat (EP 129,748) or an appetite (satiety) controlling substance for example sibutramine (GB 2,184,122 and U.S. Pat. No. 4,929,629), a cannabinoid 1 (CB1) antagonist or inverse agonist, or pharmaceutically acceptable salts, solvates, solvates of such salts or prodrugs thereof, for example rimonabant (EP 656354) and as described in WO01/70700 or a melanin concentrating hormone (MCH) antagonist, or pharmaceutically acceptable salts, solvates, solvates of such salts or prodrugs thereof, for example as described in WO 04/004726.

In another aspect of the invention, the compounds of formula I, or a pharmaceutically acceptable salt or solvate thereof, or a solvate of such a salt, may be administrated in association with an anti-inflammatory agent such as glucocorticoids, non-steroidal anti-inflammatory agents (NSAID) or intestinal anti-inflammatory agents, or pharmaceutically acceptable salts, solvates, solvates of such salts or prodrugs thereof. Suitable glucocorticoids will include, but will not be limited to betametason, dexametason, methyl prednisolon, prednisolon, prednison, triamcinolon, hydrocortison, cortison and budesonid. Suitable non-steroidal anti-inflammatory agents will include, but will not be limited to indometacin, diclofenac, ibuprofen as well as acetylsalicylic acid. Suitable intestinal anti-inflammatory agents will include, but will not be limited to amino salicylates such as sulfasalazin, mesalazin, olsalazin and balsalazid.

In another aspect of the invention, the compounds of formula I, or a pharmaceutically acceptable salt or solvate thereof, or a solvate of such a salt, may be administrated in association with a cholinesterase inhibitor or an N-methyl-D-aspartate (NMDA) receptor antagonist, or pharmaceutically acceptable salts, solvates, solvates of such salts or prodrugs thereof, such as donepezil, rivastigmin or galantamin or memantin.

Therefore in an additional feature of the invention, there is provided a method of treating and/or preventing metabolic disorders in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section or a pharmaceutically acceptable salt, solvate, solvate of such a salt or a prodrug thereof.

Therefore in an additional feature of the invention, there is provided a method for the treatment and/or prohylaxis of type 2 diabetes and its associated complications in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

Therefore in an additional feature of the invention, there is provided a method of treating and/or preventing hyperlipidemic conditions in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section or a pharmaceutically acceptable salt, solvate, solvate of such a salt or a prodrug thereof.

In an additional feature of the invention, there is provided a method for the treatment and/or prohylaxis of dyslipidemia in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of the insulin resistance syndrome in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of cardiovascular disease in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of atherosclerosis in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prohylaxis of hypercholesterolemia in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for improving reverse cholesterol transport in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for decreasing intestinal cholesterol absorption in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for increasing HDL-cholesterol levels in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for decreasing LDL-cholesterol levels in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of inflammatory conditions in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of Alzheimer's disease in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of arteriosclerosis in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for improving HDL function in a warm-blooded animal, such as man, in need of such treatment which comprises administering to said animal an effective amount of a compound of formula I, or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt or solvate thereof, or a solvate of such a salt, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt or solvate thereof, or a solvate of such a salt, and one of the other compounds described in this combination section or a pharmaceutically acceptable salt, solvate, solvate of such a salt or a prodrug thereof.

According to a further aspect of the present invention there is provided a kit comprising:

a) a compound of formula I, or a pharmaceutically acceptable salt or solvate thereof, or a solvate of such a salt, in a first unit dosage form;

b) one of the other compounds described in this combination section or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula I, or a pharmaceutically acceptable salt or solvate thereof, or a solvate of such a salt, together with a pharmaceutically acceptable diluent or carrier, in a first unit dosage form;

b) one of the other compounds described in this combination section or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the the treatment and/or prophylaxis of metabolic disorders and its associated complications in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the the treatment and/or prophylaxis of metabolic syndrome or type 2 diabetes and its associated complications in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of dyslipidemia in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of hyperlipidaemic conditions in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of cardiovascular disease in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of atherosclerosis in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of hypercholesterolemia in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for improving reverse cholesterol transport in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for decreasing intestinal cholesterol absorption in a warm-blooded animal, such as man.

According to another feature of the invention there is provided the use of a compound of the formula I, of such or a pharmaceutically acceptable salt or solvate thereof, or a solvate a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for increasing HDL-cholesterol levels in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for decreasing LDL-cholesterol levels in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of inflammatory conditions in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Alzheimer's disease in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of arteriosclerosis in a warm-blooded animal, such as man.

According to another feature of the invention there is provided the use of a compound of the formula I, or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for improving HDL function in a warm-blooded animal, such as man.

According to a further aspect of the present invention there is provided a combination treatment comprising the administration of an effective amount of a compound of the formula I, or a pharmaceutically acceptable salt or solvate thereof, or a solvate of such a salt, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

EXAMPLES

| Abbreviations | |
|---|---|
| DMF | N,N'-dimethylformamide |
| DMSO | dimethylsulfoxide |
| EtOAc | ethyl acetate |
| EtOH | ethanol |
| HPLC | high performance liquid chromatography |
| LC-MS | liquid chromatography mass spectroscopy |
| NMR | nuclear magnetic resonance |
| THF | tetrahydrofuran |
| UV | ultra violet |
| rt | room temperature |
| min. | minutes |
| b | broad |
| bs | broad singlet |
| d | doublet |
| dd | doublet of doublets |
| m | multiplet |
| s | singlet |
| t | triplet |

General Experimental Procedures

Flash column chromatography employed normal phase silica gel 60 (0.040-0.063 mm, Merck) or IST Isolute®SPE columns normal phase silica gel. Purifications were performed on either a Gilson preparative HPLC system with a UV triggered fraction collector, equipped with a ACE C8 5 µm 250 mm×20 mm column, or on a Waters preparative HPLC system equipped with a Kromasil C8 10 µm 250 mm×21.2 mm column, or on a Waters preparative HPLC system. equipped with an ACE C8 5 µm 250 mm×50 mm column or an ACE C8 5 µm 250 mm×20 mm column, or on a Waters FractionLynx HPLC system with a mass triggered fraction collector, equipped with a ACE C8 5 µm 100 mm×21.2 mm column. $^1$H NMR spectra were obtained on a Varian Unity Plus, 400 MHz, operating at 9.3 T, equipped with a 5 mm switchable probe with an inner X-coil, for solutions in CDCl$_3$ [residual CHCl$_3$ ($\delta_H$ 7.23 ppm) as internal standard], CH$_3$CN-d$_3$ [residual CH$_3$CN ($\delta_H$ 1.94 ppm) as internal standard], or DMSO-d$_6$ [residual DMSO ($\delta_H$ 2.50 ppm) as internal standard] at 300K. Chemical shifts are given in ppm. Microwave heating was performed using single node heating in a Smith Creator from Personal Chemistry, Uppsala, Sweden.

Synthesis of Starting Materials and Intermediates

3-Chloro-4-phenylfuran-2,5-dione

To an ice cold solution of phenylmaleic anhydride (5.74 mmol, 1.0 g) in thionyl chloride (6.0 mL) was added drop wise pyridine (11.4 mmol, 0.9 g). The reaction mixture was stirred for 60 min at 0° C., followed by heating to 75° C. for 20 min. The reaction mixture was cooled to room temperature and the thionyl chloride was removed in vacuo. The crude residue was suspended in toluene (10 mL), refluxed for 10 min., followed by filtration of the hot mixture. The filtrate was concentrated to give 1.15 g (96%) of the title. $^1$H NMR (400 MHz, CDCl$_3$) δ 8.05-8.00 (m, 2H), 7.59-7.51 (m, 3H).

3-Chloro-1-(2-methoxyethyl)-4-phenyl-1H-pyrrole-2,5-dione

A solution of 3-chloro-4-phenylfuran-2,5-dione (0.20 mmol, 42 mg) and 2-methoxyethylamine (0.20 mmol, 15 mg) in glacial acetic acid (1 mL) was heated in a microwave reactor at 120° C. for two min. After cooling, the solvent was evaporated at reduced pressure. The crude product was used without purification.

3-Chloro-4-phenyl-1-(pyridin-3-ylmethyl)-1H-pyrrole-2,5-dione

A solution of 3-chloro-4-phenylfuran-2,5-dione (1.00 mmol, 209 mg) and 3-(aminomethyl)-pyridine (1.00 mmol, 26 mg) in glacial acetic acid (4 mL) was heated in a microwave reactor at 120° C. for two min. After cooling, the solvent was evaporated at reduced pressure. The crude product was used without purification.

3-Chloro-1-[4-(dimethylamino)benzyl]-4-phenyl-1H-pyrrole-2,5-dione

To a solution of 3-chloro-4-phenylfuran-2,5-dione (0.20 mmol, 42 mg) and 4-dimethylaminobenzylamine dihydrochloride (0.20 mmol, 45 mg) in glacial acetic acid (1 mL) was added triethylamine (0.40 mmol). The mixture was heated in a microwave reactor at 120° C. for two min. After cooling, the solvent was evaporated at reduced pressure. The reaction mixture was purified by HPLC (95% 0.1M ammonium acetate buffer: 5% CH$_3$CN→100% CH$_3$CN).

3-Chloro-4-phenyl-1-(pyridin-2-ylmethyl)-1H-pyrrole-2,5-dione

A solution of 3-chloro-4-phenylfuran-2,5-dione (0.20 mmol, 42 mg) and 2-aminomethyl-pyridine (0.20 mmol, 22 mg) in glacial acetic acid (1 mL) was heated in a microwave reactor at 120° C. for two min. After cooling, the solvent was evaporated at reduced pressure. The crude product was used without purification.

3-Chloro-1-(3-methoxypropyl)-4-phenyl-1H-pyrrole-2,5-dione

A solution of 3-chloro-4-phenylfuran-2,5-dione (0.20 mmol, 42 mg) and 1-amino-3-methoxypropane (0.20 mmol, 18 mg) in glacial acetic acid (1 mL) was heated in a microwave reactor at 120° C. for two min. After cooling, the solvent was evaporated at reduced pressure. The crude product was used without purification.

Methyl 4-[(3-chloro-2,5-dioxo-4-phenyl-2,5-dihydro-1H-pyrrol-1-yl)methyl]benzoate A solution of 3-chloro-4-phenylfuran-2,5-dione (0.24 mmol, 50 mg) and methyl 4-(aminomethyl)benzoate (0.24 mmol, 40 mg) in glacial acetic acid (1 mL) was heated in a microwave reactor at 120° C. for two min. After cooling, the solvent was evaporated at reduced pressure. The crude product was used without purification.

3-Chloro-1-[2-(methylthio)ethyl]-4-phenyl-1H-pyrrole-2,5-dione

A solution of 3-chloro-4-phenylfuran-2,5-dione (1.00 mmol, 209 mg) and 2-aminoethyl methyl sulphide (1.00 mmol, 91 mg) in glacial acetic acid (2 mL) was heated in a microwave reactor at 120° C. for two min. After cooling, the solvent was evaporated at reduced pressure. The residue was partitioned between water and $CH_2Cl_2$. The organic phase was evaporated and the crude product was purified by HPLC (95% 0.1M ammonium acetate buffer: 5% $CH_3CN \rightarrow 100\%$ $CH_3CN$) to give 152 mg (54%) of the title compound. $^1H$ NMR (400 MHz, $CDCl_3$): δ 7.97-7.90 (m, 2H), 7.53-7.47 (m, 3H), 3.86 (t, J=6.8 Hz, 2H), 2.78 (t, J=6.8 Hz, 2H), 2.16 (s, 3H).

3-Hydroxy-4-phenyl-1H-pyrrole-2,5-dione

Prepared according to literature procedure: C. S. Rooney, et al; J. Med. Chem., Vol. 26 (1983) pp 700-714.

3-Chloro-4-phenyl-1H-pyrrole-2,5-dione

To a suspension of 3-hydroxy-4-phenyl-1H-pyrrole-2,5-dione (25.0 g, 0.13 mol) in dichloromethane (600 mL) under nitrogen was added DMF (36 mL). The suspension was cooled to ice temperature and treated with oxalyl chloride (40.0 g, 0.32 mol). The reaction mixture was subsequently refluxed overnight. After cooling to room temperature silica gel was added and the reaction mixture evaporated to dryness and subjected to flash chromatography (hexane:EtOAc 80:20). Trituration with dichloromethane, filtration and drying gave 17.6 g (64%) of the title compound. $^1H$ NMR (400 MHz, $CDCl_3$) δ 7.96-7.89 (m, 2H), 7.88-7.77 (bs, 1H), 7.55-7.45 (m, 3H).

3-[(4-Methoxyphenyl)amino]-4-phenyl-1H-pyrrole-2,5-dione

To a solution of 3-chloro-4-phenyl-1H-pyrrole-2,5-dione (4.84 mmol, 1.0 g) in dry DMF (5 mL) was added 4-methoxyaniline (4.87 mmol, 600 mg) and the reaction mixture was subjected to microwave heating single node 150° C., 15 min, followed by 150° C., 10 min. The solvent was evaporated, and the crude mixture was partitioned between dichloromethane and water. The organic phase was dried over anhydrous $Na_2SO_4$, concentrated and the residue was purified on $SiO_2$ (Heptane:EtOAc, 3:1→2:1) to give 457 mg (32%) of the title compound. $^1H$ NMR (400 MHz, DMSO-$d_6$) δ 10.62 (s, 1H), 9.27 (s, 1H), 7.09-6.99 (m, 3H), 6.87-6.83 (m, 2H), 6.65-6.60 (m, 2H), 6.52-6.47 (m, 2H), 3.58 (s, 3H).

3-Phenyl-4-{[4-(trifluoromethoxy)phenyl]amino}-1H-pyrrole-2,5-dione

3-Chloro-4-phenyl-1H-pyrrole-2,5-dione (2.00 mmol, 415 mg), 4-difluoromethoxyaniline (2.00 mmol, 354 mg) and triethylamine (2.00 mmol, 202 mg) were dissolved in DMF (5 mL). The mixture was stirred at 70° C. for 20 hours. After cooling, the reaction mixture was filtrated and purified by HPLC (95% 0.1M ammonium acetate buffer: 5% $CH_3CN \rightarrow 100\%$ $CH_3CN$) to give 320 mg (46%) of the title compound. $^1H$ NMR (400 MHz, $CDCl_3$): δ 7.22 (bs, 1H), 7.22-7.09 (m, 3H), 7.02-6.97 (m, 2H), 6.91-6.85 (m, 2H), 6.69-6.63 (m, 2H).

tert-Butyl [5-(bromomethyl)pyridin-2-yl]carbamate

Prepared according to literature procedure: WO0066557 Linschoten, M. et al, Astrazeneca A B, Nov. 9, 2000.

tert-Butyl {5-[(3-chloro-2,5-dioxo-4-phenyl-2,5-dihydro-1H-pyrrol-1-yl)methyl]pyridin-2-yl}carbamate 3-Chloro-4-phenyl-1H-pyrrole-2,5-dione (1.55 g, 7.47 mmol) was dissolved in DMF (25 mL) under nitrogen atmosphere and cooled in an ice-bath. tert-Butyl [5-(bromomethyl)pyridin-2-yl]carbamate (2.14 g, 7.46 mmol) was added followed by anhydrous potassium carbonate (1.03 g, 7.47 mmol) and the mixture was stirred for one and a half hours whereafter the cooling-bath was removed. The mixture was stirred for another two hours and then neutralized with 1% HCl. Water (100 mL) was added and the mixture was extracted with $CH_2Cl_2$ (50 mL×3). The extracts were combined, washed with water (100 mL×2), dried with magnesium sulphate, filtered and evaporated. The crude product (3.41 g) was used without further purification. $^1H$ NMR (400 MHz, $CDCl_3$): δ 8.32 (d, J=2 Hz, 1H), 7.92-7.89 (m, 3H), 7.83 (bs, 1H), 7.72 (dd, J=9, 2 Hz, 1H), 7.49-7.47 (m, 3H), 4.71 (s, 2H), 1.52 (s, 9H).

EXAMPLES

Example 1

1-(2-Methoxyethyl)-3-[(4-methoxyphenyl)amino]-4-phenyl-1H-pyrrole-2,5-dione

3-Chloro-1-(2-methoxyethyl)-4-phenyl-1H-pyrrole-2,5-dione (0.20 mmol, 53 mg) and 4-methoxyaniline (0.48 mmol, 59 mg) were dissolved in DMF (1 mL). The mixture was heated in a microwave reactor at 150° C. for five min.min. After cooling, the reaction mixture was purified by HPLC (95% 0.1M ammonium acetate buffer: 5% $CH_3CN \rightarrow 100\%$ $CH_3CN$) to give 15 mg (21%) of the title compound. $^1H$ NMR (400 MHz, $CDCl_3$): δ 7.27 (bs, 1H), 7.13-7.04 (m, 3H), 7.00-6.96 (m, 2H), 6.61-6.50 (m, 4H), 3.80 (t, J=5.6 Hz, 2H), 3.67 (s, 3H), 3.62 (t, J=5.6 Hz, 2H), 3.36 (s, 3H).

Example 2

3-{[4-(Difluoromethoxy)phenyl]amino}-1-(2-methoxyethyl)-4-phenyl-1H-pyrrole-2,5-dione 3-Chloro-1-(2-methoxyethyl)-4-phenyl-1H-pyrrole-2,5-dione (0.13 mmol, 36 mg) and 4-difluoromethoxyaniline (0.28 mmol, 45 mg) were dissolved in DMF (1 mL). The mixture was heated in a microwave reactor at 150° C. for 20 min. After cooling, the reaction mixture was purified by HPLC (95% 0.1M ammonium acetate buffer: 5% $CH_3CN \rightarrow 100\%$ $CH_3CN$) to give 13 mg (24%) of the title compound. $^1H$ NMR (400 MHz, $CDCl_3$): δ 7.25 (bs, 1H), 7.19-7.08 (m, 3H), 7.02-6.97 (m, 2H), 6.81-6.75 (m, 2H), 6.66-6.60 (m, 2H), 6.36 (t, J=74.0 Hz, 1H), 3.83 (t, J=5.7 Hz, 2H), 3.63 (t, J=5.7 Hz, 2H), 3.38 (s, 3H)

Example 3

N-(4-{[2,5-Dihydro-1-(2-methoxyethyl)-2,5-dioxo-4-phenyl-1H-pyrrol-3-yl]amino}phenyl)-acetamide 3-Chloro-1-(2-methoxyethyl)-4-phenyl-1H-pyrrole-2,5-dione (0.26 mmol, 70 mg) and 4-aminoacetanilide (0.53 mmol, 79 mg) was dissolved in dry $CH_3CN$ (2 mL) and the reaction mixture was subjected twice to microwave heating single node 140° C. for 10 min. 0.3 mL Water was added and the reaction mixture was purified using HPLC (57% 0.1M ammonium acetate buffer: 43% $CH_3CN \rightarrow 100\%$ $CH_3CN$, 20 mL/min) to give 45 mg (45%) of the title compound. $^1H$ NMR (400 MHz, $CD_3CN$) δ 8.17 (bs, 1H), 7.78 (bs, 1H), 7.24-7.09 (m, 5H), 7.04-7.00 (m, 2H), 6.73-6.68 (m, 2H), 3.73 (t, J=5.7 Hz, 2H), 3.59 (t, J=5.7 Hz, 2H), 3.33 (s, 3H), 2.01 (s, 3H).

Example 4

1-(2-Methoxyethyl)-3-{[4(methylthio)phenyl]amino}-4-phenyl-1H-pyrrole-2,5-dione

3-Chloro-1-(2-methoxyethyl)-4-phenyl-1H-pyrrole-2,5-dione (0.26 mmol, 70 mg) and 4-(methylthio)aniline (0.53 mmol, 73 mg) was dissolved in dry $CH_3CN$ (2 mL) and the reaction mixture was sequentially subjected to microwave heating single node 140° C. for, 10 min, 140° C. for 10 min, and 140° C. for 20 min. 0.3 mL Water was added and the reaction mixture was purified using HPLC (57% 0.1M ammonium acetate buffer: 43% $CH_3CN \rightarrow 100\%$ $CH_3CN$, 20 mL/min) to give 49 mg (50%) of the title compound. $^1H$ NMR (400 MHz, $CDCl_3$) δ 7.22 (bs, 1H), 7.19-7.10 (m, 3H), 7.06-7.00 (m, 2H), 6.95-6.90 (m, 2H), 6.58-6.53 (m, 2H), 3.82 (t, J=5.6 Hz, 2H), 3.63 (t, J=5.6 Hz, 2H), 3.38 (s, 3H), 2.38 (s, 3H).

Example 5

3-[(2-Acetyl-5-benzofuranyl)amino]-1-(2-methoxyethyl)-4-phenyl-1H-pyrrole-2,5-dione 3-Chloro-1-(2-methoxyethyl)-4-phenyl-1H-pyrrole-2,5-dione (0.26 mmol, 70 mg) and 1-(5-aminobenzo[b]furan-2-yl)ethan-1-one (0.53 mmol, 92 mg) was dissolved in dry $CH_3CN$ (2 mL) and the reaction mixture was subjected to microwave heating single node 150° C. for 15 min and purified on $SiO_2$ (EtOAc:heptane, 1:1) to give 18 mg (15%) of the title compound. $^1H$ NMR (400 MHz, $CDCl_3$) δ 7.53 (bs, 1H), 7.40 (d, 1H), 7.24-7.09 (m, 5H), 7.06 (dd, 1H), 6.92 (d, 1H), 3.98 (t, J=5.6 Hz, 2H), 3.78 (t, J=5.6 Hz, 2H), 3.52 (s, 3H), 2.69 (s, 3H).

Example 6

1-(2-Methoxyethyl)-3-[(4-morpholin-4-ylphenyl)amino]-4-phenyl-1H-pyrrole-2,5-dione 3-Chloro-1-(2-methoxyethyl)-4-phenyl-1H-pyrrole-2,5-dione (0.26 mmol, 70 mg) and 4-morpholinoaniline (0.53 mmol, 94 mg) was dissolved in dry $CH_3CN$ (2 mL) and the reaction mixture was subjected to microwave heating single node 130° C. for 10 min and purified on $SiO_2$ (EtOAc:heptane, 1:1) to give 96 mg (89%) of the title compound. $^1H$ NMR (400 MHz, $CD_3CN$) δ 7.73 (bs, 1H), 7.17-7.04 (m, 3H), 6.98-6.93 (m, 2H), 6.70-6.64 (m, 2H), 6.59-6.54 (m, 2H), 3.75-3.70 (m, 6H), 3.58 (t, J=5.6 Hz, 2H), 3.33 (s, 3H), 2.98-2.95 (m, 4H).

Example 7

3-[(4-Morpholin-4-ylphenyl)amino]-4-phenyl-1-(pyridin-3-ylmethyl)-1H-pyrrole-2,5-dione 4-Morpholinoaniline (0.94 mmol, 178 mg) dissolved in dry $CH_3CN$ (2 mL) was added to crude 3-chloro-4-phenyl-1-(pyridin-3-ylmethyl)-1H-pyrrole-2,5-dione (0.47 mmol, 140 mg) and the reaction mixture was subjected to microwave heating single node 130° C. for 10 min. 0.3 mL water was added and the reaction mixture was purified using HPLC (57% 0.1M ammonium acetate buffer: 43% $CH_3CN \rightarrow 100\%$ $CH_3CN$, 20 mL/min) to give 56 mg (27%) of the title compound. $^1H$ NMR (400 MHz, $CD_3CN$) δ 8.63 (d, 1H), 8.51 (dd, 1H), 7.81-7.73 (m, 1H), 7.36-7.31 (m, 1H), 7.16-7.11 (m, 1H), 7.10-7.04 (m, 2H), 6.99-6.93 (m, 2H), 6.69-6.64 (m, 2H), 6.59-6.53 (m, 2H), 4.75 (s, 2H), 3.74 (t, J=4.8 Hz, 4H), 2.97 (t, J=4.8 Hz, 4H).

Example 8

3-[(2-Acetyl-5-benzofuranyl)amino]-4-phenyl-1-(pyridin-3-ylmethyl)-1H-pyrrole-2,5-dione 1-(5-Aminobenzo[b]furan-2-yl)ethan-1-one (0.94 mmol, 164 mg) dissolved in dry $CH_3CN$ (2 mL) was added to crude 3-chloro-4-phenyl-1-(pyridin-3-ylmethyl)-1H-pyrrole-2,5-dione (0.47 mmol, 140 mg) and the reaction mixture was subjected to microwave heating single node 130° C. for 10 min. 0.3 mL water was added and the reaction mixture was purified using HPLC (57% 0.1M ammonium acetate buffer: 43% $CH_3CN \rightarrow 100\%$ $CH_3CN$, 20 mL/min) to give 15 mg (7%) of the title compound. $^1H$ NMR (400 MHz, $CD_3CN$) δ 8.64 (d, 1H), 8.52 (dd, 1H), 8.01 (bs, 1H), 7.80-7.75 (m, 1H), 7.35 (dd, 1H), 7.31-7.23 (m, 2H), 7.08-6.93 (m, 7H), 4.77 (s, 2H), 2.50 (s, 3H).

Example 9

3-Phenyl-1-(pyridin-3-ylmethyl)-4-{[4-(trifluoromethoxy)phenyl]amino}-1H-pyrrole-2,5-dione 4-(Trifluoromethoxy)aniline (0.94 mmol, 177 mg) dissolved in dry $CH_3CN$ (2 mL) was added to crude 3-chloro-4-phenyl-1-(pyridin-3-ylmethyl)-1H-pyrrole-2,5-dione (0.47 mmol, 140 mg) and the reaction mixture was sequentially subjected to microwave heating single node 140° C. for 20 min, 140° C. for 120 min, and 140° C. for 120 min. 0.3 mL Water was added and the reaction mixture was purified using HPLC (57% 0.1M ammonium acetate buffer: 43% $CH_3CN \rightarrow 100\%$ $CH_3CN$, 20 mL/min) to give 92 mg (45%) of the title compound. $^1H$ NMR (400 MHz, $CD_3CN$) δ 8.63 (d, 1H), 8.52 (dd, 1H), 7.95 (bs, 1H), 7.80-7.74 (m, 1H), 7.37-7.32 (m, 1H), 7.19-7.08 (m, 3H), 7.01-6.95 (m, 2H), 6.94-6.88 (m, 2H), 6.84-7.78 (m, 2H), 4.77 (s, 2H).

Example 10

3-[(4-Methoxyphenyl)amino]-4-phenyl-1-(pyridin-3-ylmethyl)-1H-pyrrole-2,5-dione

To a solution of 3-chloro-4-phenyl-1-(pyridin-3-ylmethyl)-1H-pyrrole-2,5-dione (0.50 mmol, 149 mg) in DMF (1 mL) was added 4-methoxyaniline (1.10 mmol, 135 mg) The mixture was heated in a microwave reactor at 150° C. for five min. After cooling, the reaction mixture was purified by HPLC (95% 0.1M ammonium acetate buffer: 5% $CH_3CN \rightarrow 100\%$ $CH_3CN$) to give 77 mg (40%) of the title compound. $^1H$ NMR (400 MHz, $CDCl_3$) δ 8.71 (d, J=1.8 Hz, 1H), 8.54 (dd, $J_1$=4.7 Hz, $J_2$=1.6 Hz, 1H), 7.80-7.75 (m, 1H), 7.35 (bs, 1H), 7.26 (dd, $J_1$=7.8 Hz, $J_2$=4.7 Hz, 1H), 7.15-7.05 (m, 3H), 6.98-6.94 (m, 2H), 6.62-6.50 (m, 4H), 4.78 (s, 2H), 3.68 (s, 3H).

Example 11

3-Anilino-4-phenyl-1-(pyridin-3-ylmethyl)-1H-pyrrole-2,5-dione

To a solution of 3-chloro-4-phenyl-1-(pyridin-3-ylmethyl)-1H-pyrrole-2,5-dione (0.25 mmol, 75 mg) in DMF (0.5 mL) was added aniline (0.55 mmol, 51 mg). The mixture was heated in a microwave reactor at 150° C. for five min. After cooling, the reaction mixture was purified by HPLC (95% 0.1M ammonium acetate buffer: 5% $CH_3CN \rightarrow 100\%$ $CH_3CN$) to give 38 mg (43%) of the title compound. $^1H$ NMR (400 MHz, $CDCl_3$) δ 8.72 (bs, 1H), 8.54 (d, br, 1H), 7.79-7.75 (m, 1H), 7.47 (bs, 1H), 7.29-7.23 (m, 1H), 7.17-7.06 (m, 3H), 7.04-6.93 (m, 5H), 6.66-6.60 (m, 2H), 4.79 (s, 2H).

Example 12

3-{[4-(Difluoromethoxy)phenyl]amino}-4-phenyl-1-(pyridin-3-ylmethyl)-1H-pyrrole-2,5-dione 4-(Difluoromethoxy)aniline (0.94 mmol, 149 mg) dissolved in dry $CH_3CN$ (2.3 mL) was added to crude 3-chloro-4-phenyl-1-(pyridin-3-ylmethyl)-1H-pyrrole-2,5-dione (0.39 mmol, 115 mg) and the reaction mixture was subjected to microwave heating single node 140° C., one h. The reaction mixture was purified using HPLC (57% 0.1M ammonium acetate buffer: 43% $CH_3CN \rightarrow 100\%$ $CH_3CN$, 20 mL/min) to give 122 mg (75%) of the title compound. $^1H$ NMR (400 MHz, $CD_3CN$) δ 8.63 (d, 1H), 8.51 (dd,1H), 7.92 (bs, 1H), 7.79-7.74 (m, 1H), 7.34 (dd, 1H), 7.20-7.07 (m, 3H), 7.00-6.94 (m, 2H), 6.78 (s, 4H), 6.59 (t, J=74.1 Hz, 1H), 4.76 (s, 2H).

Example 13

1-[4-(Dimethylamino)benzyl]-3-[(4-methoxyphenyl)amino]-4-phenyl-1H-pyrrole-2,5-dione 3-Chloro-1-[4-(dimethylamino)benzyl]-4-phenyl-1H-pyrrole-2,5-dione (0.20 mmol, 68 mg) and 4-methoxyaniline (0.48 mmol, 59 mg) were dissolved in DMF (1 mL). The mixture was heated in a microwave reactor at 150° C. for five min. After cooling, the reaction mixture was purified by HPLC (95% 0.1M ammonium acetate buffer: 5% $CH_3CN \rightarrow 100\%$ $CH_3CN$) to give 11 mg (13%) of the title compound. $^1H$ NMR (400 MHz, $CDCl_3$) δ 7.38-7.34 (m, 2H), 7.15 (bs, 1H), 7.13-7.04 (m, 3H), 6.97 (m, 2H), 6.70 (d, 2H), 6.60-6.51 (m, 4H), 4.67 (s, 2H), 3.69 (s, 3H), 2.93 (s, 6H).

Example 14

3-[(4-Methoxyphenyl)amino]-4-phenyl-1-(pyridin-4-ylmethyl)-1H-pyrrole-2,5-dione A mixture of 3-[(4-methoxyphenyl)amino]-4-phenyl-1H-pyrrole-2,5-dione (0.50 mmol, 147 mg), 4-hydroxymethylpyridine (0.75 mmol, 82 mg), diethyl azodicarboxylate (0.75 mmol, 131 mg) and triphenylphosphine (0.75 mmol, 197 mg) in dry THF (2 mL) was heated in a microwave reactor at 120° C. for five min. After cooling, the reaction mixture was purified by HPLC (95% 0.1M ammonium acetate buffer: 5% $CH_3CN \rightarrow 100\%$ $CH_3CN$) to give 56 mg (29%) of the title compound. $^1H$ NMR (400 MHz, $CDCl_3$) δ 8.59 (bs, 2H), 7.35-7.29 (m, br, 2H), 7.25 (s, br, 1H), 7.17-7.06 (m, 3H), 7.01-6.96 (m, 2H), 6.63-6.53 (m, 4H), 4.77 (s, 2H), 3.70 (s, 3H).

Example 15

3-[(4-Methoxyphenyl)amino]-4-phenyl-1-(pyridin-2-ylmethyl)-1H-pyrrole-2,5-dione 3-Chloro-4-phenyl-1-(pyridin-2-ylmethyl)-1H-pyrrole-2,5-dione (2.39 mmol, 714 mg) and 4-methoxyaniline (5.26 mmol, 648 mg) were dissolved in DMF (4 mL). The mixture was heated in a microwave reactor at 150° C. for five min. After cooling, the reaction mixture was purified by HPLC (95% 0.1M ammonium acetate buffer: 5% $CH_3CN \rightarrow 100\%$ $CH_3CN$) to give 710 mg (77%) of the title compound. $^1H$ NMR (400 MHz, $CDCl_3$): 8.60-8.57 (m, 1H), 7.71-7.65 (m, 1H), 7.36-7.30 (m, 1H), 7.24 (bs, 1H), 7.23-7.19 (m, 1H), 7.13-7.05 (m, 3H), 7.04-6.99 (m, 2H), 6.64-6.53 (m, 4H), 4.95 (s, 2H), 3.70 (s, 3H).

Example 16

3-[(4-Methoxyphenyl)amino]-1-(3-methoxypropyl)-4-phenyl-1H-pyrrole-2,5-dione 3-Chloro-1-(3-methoxypropyl)-4-phenyl-1H-pyrrole-2,5-dione (0.20 mmol, 56 mg) and 4-methoxyaniline (0.48 mmol, 59 mg) were dissolved in DMF (1 mL). The mixture was heated in a microwave reactor at 150° C. for five min. After cooling, the reaction mixture was purified by HPLC (95% 0.1M ammonium acetate buffer: 5% $CH_3CN \rightarrow 100\%$ $CH_3CN$) to give 11 mg (15%) of the title compound. $^1H$ NMR (400 MHz, $CDCl_3$) δ 7.17 (bs, 1H), 7.14-7.05 (m, 3H), 7.01-6.95 (m, 2H), 6.63-6.52 (m, 4H), 3.71 (t, J=7.0 Hz, 2H), 3.70 (s, 3H), 3.45 (t, J=6.2 Hz, 2H), 3.34 (s, 3H), 1.94 (m, 2H).

Example 17

Methyl 4-({3-[(4-methoxyphenyl)amino]-2,5-dioxo-4-phenyl-2,5-dihydro-1H-pyrrol-1-yl}methyl)benzoate Methyl 4-[(3-chloro-2,5-dioxo-4-phenyl-2,5-dihydro-1H-pyrrol-1-yl)methyl]benzoate (0.24 mmol, 85 mg), 4-methoxyaniline (0.26 mmol, 33 mg) and triethylamine (0.29 mmol, 29 mg) were dissolved in DMF (1 mL). The mixture was heated in a microwave reactor at 150° C. for five min. After cooling, the reaction mixture was purified by HPLC (95% 0.1M ammonium acetate buffer: 5% $CH_3CN \rightarrow 100\%$ $CH_3CN$) to give 32 mg (30%) of the title compound. $^1H$ NMR (400 MHz, $CDCl_3$) δ 8.03-7.99 (m, 2H), 7.52-7.46 (m, 2H), 7.21 (bs, 1H), 7.16-7.05 (m, 3H), 7.01-6.95 (m, 2H), 6.62-6.52 (m, 4H), 4.81 (s, 2), 3.90 (s, 3H), 3.69 (s, 3H).

Example 18

3-[(4-Methoxyphenyl)amino]-1-[2-(methylthio)ethyl]-4-phenyl-1H-pyrrole-2,5-dione 3-Chloro-1-[2-(methylthio)ethyl]-4-phenyl-1H-pyrrole-2,5-dione (0.40 mmol, 113 mg) and 4-methoxyaniline (0.88 mmol, 109 mg) were dissolved in DMF (1 mL). The mixture was heated in a microwave reactor at 150° C. for 10 min. After cooling, the solvent was evaporated under reduced pressure. The residue was partitioned between water and $CH_2Cl_2$. The organic phase was evaporated and purified by flash chromatography using a pre-packed silica column. The desired product was eluted with heptane/EtOAc 2:1. Yield 118 mg (80%) .$^1H$ NMR (400MHz, $CDCl_3$) δ 7.26 (bs, 1H), 7.15-7.06 (m, 3H), 7.01-6.96 (m, 2H), 6.63-6.52 (m, 4H), 3.83 (t, J=7.0 Hz, 2H), 3.69 (s, 3H), 2.79 (t, J=7.0 Hz, 2H), 2.18 (s, 3H).

Example 19

3-[(4-Methoxyphenyl)amino]-4-phenyl-1-(3,3,3-trifluoropropyl)-1H-pyrrole-2,5-dione To a solution of 3-[(4-methoxyphenyl)amino]-4-phenyl-1H-pyrrole-2,5-dione (0.17 mmol, 50 mg), 3,3,3-trifluoropropan-1-ol (0.19 mmol, 21 mg), diethyl azodicarboxylate (0.19 mmol, 33 mg) in dry THF (1 mL) was added triphenylphosphine (0.19 mmol, 49 mg) in dry THF (1 mL). The mixture was heated in a microwave reactor at 130° C. for six min. After cooling, the reaction mixture was purified by HPLC (95% 0.1M ammonium acetate buffer: 5% $CH_3CN \rightarrow 100\%$ $CH_3CN$) to give 51 mg (77%) of the title compound. $^1$H NMR (400 MHz, $CDCl_3$) δ 7.27 (bs, 1H), 7.17-7.06 (m, 3H), 7.00-6.95 (m, 2H), 6.64-6.55 (m, 4H), 3.89 (t, J=7.3 Hz, 2H), 3.70 (s, 3H), 2.61-2.48 (m, 2H).

Example 20

1-(3-Furylmethyl)-3-[(4-methoxyphenyl)amino]-4-phenyl-1H-pyrrole-2,5-dione

To a solution of 3-[(4-methoxyphenyl)amino]-4-phenyl-1H-pyrrole-2,5-dione (0.17 mmol, 50 mg), 3-furanmethanol (0.19 mmol, 18 mg), diethyl azodicarboxylate (0.19 mmol, 33 mg) in dry THF (1 mL) was added triphenylphosphine (0.19 mmol, 49 mg) in dry THF (1 mL). The mixture was heated in a microwave reactor at 130° C. for six min. After cooling, the reaction mixture was purified by HPLC (95% 0.1M ammonium acetate buffer: 5% $CH_3CN \rightarrow 100\%$ $CH_3CN$) to give 17 mg (27%) of the title compound. $^1$H NMR (400 MHz, $CDCl_3$) δ 7.61 (bs, 1H), 7.35 (bs, 1H), 7.16 (bs, 1H), 7.15-7.05 (m, 3H), 7.00-6.95 (m, 2H), 6.62-6.51 (m, 4H), 6.48 (bs, 1H), 4.63 (s, 2H), 3.69 (s, 3H).

Example 21

3-[(4-Methoxyphenyl)amino]-4-phenyl-1-(2,2,2-trifluoroethyl)-1H-pyrrole-2,5-dione A solution of 3-[(4-methoxyphenyl)amino]-4-phenyl-1H-pyrrole-2,5-dione (2.11 mmol, 620 mg), diethyl azodicarboxylate (2.11 mmol, 367 mg) and triphenylphosphine (2.11 mmol, 553 mg) in dry THF (2 mL) was prepared in sealed reaction vessel. 2,2,2-trifluoroethanol (2.11 mmol, 211 mg) was added. The mixture was stirred at 40° C. for 19 hours. Acetonitrile was added until some triphenylphosphine oxide was precipitated. The reaction mixture was filtered and purified by HPLC (95% 0.1M ammonium acetate buffer: 5% $CH_3CN \rightarrow 100\%$ $CH_3CN$) to give 260 mg (33%) of the title compound. $^1$H NMR (400 MHz, $CDCl_3$) δ 7.30 (bs, 1H), 7.18-7.06 (m, 3H), 7.01-6.96 (m, 2H), 6.64-6.52 (m, 4H), 4.23 (q, J=8.8 Hz, 2H), 3.70 (s, 3H).

Example 22

3-[(4-Methoxyphenyl)amino]-1-[(5-methylisoxazol-3-yl)methyl]-4-phenyl-1H-pyrrole-2,5-dione To a solution of 3-[(4-methoxyphenyl)amino]-4-phenyl-1H-pyrrole-2,5-dione (0.17 mmol, 50 mg), 5-methylisoxazole-3-methanol (0.19 mmol, 21 mg) and diethyl azodicarboxylate (0.19 mmol, 33 mg) in dry THF (1 mL) was added triphenylphosphine (0.19 mmol, 49 mg) in dry THF (1 mL). The mixture was heated in a microwave reactor at 130° C. for six min. After cooling, the reaction mixture was purified by HPLC (95% 0.1M ammonium acetate buffer: 5% $CH_3CN \rightarrow 100\%$ $CH_3CN$) to give 14 mg (21%) of the title compound. $^1$H NMR (400 MHz, $CDCl_3$) δ 7.23 (bs, 1H), 7.16-7.06 (m, 3H), 7.01-6.96 (m, 2H), 6.63-6.53 (m, 4H), 6.03 (d, J=0.7 Hz, 1H), 4.82 (s, 2H), 3.70 (s, 3H), 2.39 (d, J=0.7 Hz, 3H).

Example 23

Ethyl {3-[(4-methoxyphenyl)amino]-2,5-dioxo-4-phenyl-2,5-dihydro-1H-pyrrol-1-yl}acetate To a solution of 3-[(4-methoxyphenyl)amino]-4-phenyl-1H-pyrrole-2,5-dione (0.34 mmol, 100 mg) in dry THF (1.0 mL) under an atmosphere of $N_2$ at room temperature was added ethyl glycolate (0.34 mmol, 35 mg). The reaction mixture was cooled to 0° C. and tributylphosphine (0.17 mmol, 34 mg) was added followed by 1,1'-(azodicarbonyl)dipiperidine (0.36 mmol, 84 mg). After stirring at 0° C. for 10 min., the reaction mixture was brought to room temperature and the stirring was continued for 26 h. The reaction mixture was diluted with $CH_3CN$:water 1:1 (2 mL) and purified using HPLC (95% 0.1M ammonium acetate buffer:5% $CH_3CN \rightarrow 100\%$ $CH_3CN$, 38.5 min., 25 mL/min.) to give 53 mg (41%) of the title compound. $^1$H NMR (400 MHz, $CDCl_3$) δ 7.22-7.17 (bs, 1H), 7.15-7.05 (m, 3H), 7.01-6.96 (m, 2H), 6.63-6.52 (m, 4H), 4.36 (s, 2H), 4.24 (q, J=7.1 Hz, 2H), 3.69 (s, 3H), 1.30 (t, J=7.1 Hz, 3H).

Example 24

3-Phenyl-1-(2,2,2-trifluoroethyl)-4-{[4-(trifluoromethoxy)phenyl]amino}1H-pyrrole-2,5-dione A mixture of 3-phenyl-4-{[4-(trifluoromethoxy)phenyl]amino}-1H-pyrrole-2,5-dione (0.63 mmol, 220 mg), diethyl azodicarboxylate (0.70 mmol, 121 mg) and triphenylphosphine (0.70 mmol, 182 mg) in dry THF (4 mL) was prepared in sealed reaction vessel. 2,2,2-Trifluoroethanol (0.70 mmol, 70 mg) was added. The mixture was first stirred at rt. for three days, then at 40° C. for two hours and finally at 100° C. for 30 min. in a microwave reactor. The reaction mixture was filtered and purified by HPLC (95% 0.1M ammonium acetate buffer: 5% $CH_3CN \rightarrow 100\%$ $CH_3CN$) to give 7 mg (3%) of the title compound. $^1$H NMR (400 MHz, $CDCl_3$) δ 7.45 (s, br, 1H), 7.22-7.09 (m, 3H), 7.02-6.97 (m, 2H), 6.92-6.84 (m, 2H), 6.70-6.65 (m, 2H), 4.24 (q, J=8.6 Hz, 2H).

Example 25

1-[(6-Aminopyridin-3-yl)methyl]-3-[(4-methoxyphenyl)amino]-4-phenyl-1H-pyrrole-2,5-dione To a solution of tert-butyl {5-[(3-chloro-2,5-dioxo-4-phenyl-2,5-dihydro-1H-pyrrol-1-yl)methyl]pyridin-2-yl}carbamate (0.86 mmol, 357 mg) in dry DMF (1.0 mL) was added 4-methoxyaniline (0.96 mmol, 118 mg) and anhydrous potassium carbonate (0.96 mmol, 133 mg) and the reaction mixture was subjected to microwave heating single node at 150° C. for 15 min. The reaction mixture was purified using HPLC (95% 0.1M ammonium acetate buffer:5% $CH_3CN \rightarrow 5\%$ 0.1M ammonium acetate buffer: 95% $CH_3CN$, 10 min., 25 mL/min.) to give 102 mg (29%) of the title compound. $^1$H NMR (400 MHz, $CDCl_3$) δ 8.03 (s, 1H), 7.62

(dd, J=8.6 Hz, J=2.3 Hz, 1H), 7.21 (bs, 1H), 7.15-7.04 (m, 3H), 6.98-6.93 (m, 2H), 6.62-6.49 (m, 5H), 4.62 (s, 2H), 3.69 (s, 3H).

Example 26

1-[(6-Aminopyridin-3-yl)methyl]-3-{[4-(difluoromethoxy)phenyl]amino}-4-phenyl-1H-pyrrole-2,5-dione A mixture of tert-butyl {5-[(3-chloro-2,5-dioxo-4-phenyl-2,5-dihydro-1H-pyrrol-1-yl)methyl]pyridin-2-yl}carbamate (0.70 g, 1.7 mmol) and 4-(difluoromethoxy)-aniline (0.54 g, 3.4 mmol) in DMF (4 mL) was heated in a microwave reactor at 150° C. for eight min. The solvent was evaporated and the residue was purified on a column (Isolute® SI, 10 g/70 mL), using $CH_2Cl_2$ and then $CH_3OH/CH_2Cl_2$ (1:99, 2:98 and then 5:95) as eluant, to give 0.4 g (54%) of the title compound. $^1H$ NMR (400 MHz, $CDCl_3$) δ 7.99 (bs, 1H), 7.67-7.62 (m, 2H), 7.14-7.04 (m, 3H), 6.91 (d, J=8 Hz, 2H), 6.78 (d, J=8 Hz, 1H), 6.72 (d, J=9 Hz, 2H), 6.63 (d, J=9 Hz, 2H), 6.33 (t, J=74 Hz, 1H), 4.60 (s, 2H).

Example 27

1-[(6-Aminopyridin-3-yl)methyl]-3-[(4-morpholin-4-ylphenyl)amino]-4-phenyl-1H-pyrrole-2,5-dione A mixture of tert-Butyl {5-[(3-chloro-2,5-dioxo-4-phenyl-2,5-dihydro-1H-pyrrol-1-yl)methyl]pyridin-2-yl}carbamate (0.85 g, 2.06 mmol) and 4-morpholinoaniline (0.73 g, 4.12 mmol) in DMF (4 mL) was heated in a microwave reactor at 150° C. for 10 min. Preparative HPLC (C18, 50×250 mm, 60% 0.1M ammonium acetate buffer: 40% $CH_3CN$→100% $CH_3CN$) gave 0.39 g (42%) of the title compound. $^1H$ NMR (400 MHz, $CDCl_3$) δ 8.14 (bs, 1H), 7.55 (dd, J=8, 2 Hz, 1H), 7.28-7.23 (br, 1H), 7.13-7.04 (m, 3H), 6.95 (dd, J=8, 2 Hz, 2H), 6.57-6.51 (m, 4H), 6.44 (d, J=8 Hz, 1H), 4.62 (s, 2H), 4.62-4.53 (br, 2H), 3.81-3.79 (m, 4H), 3.01-2.98 (m, 4H).

Biological Activity Co-Activator Recruitment Assay

The Ligand Binding Domain (LBD) of human LXRalpha (amino acid 205-447) and LXRbeta (amino acid 216-461) was produced by recombinant techniques in *E coli*. A fragment of the human Steroid Receptor Co-Activator-1 (SRC-1) was produced as a synthetic peptide. An anti-6His-antibody coupled with Europium ($Eu^{3+}$) was used to recognize the His-tag on the LXR-LBD and Allophycocyanin (APC) coupled to streptavidin was used to recognize the biotinylated SRC-1. Agonist binding to LXRalpha or LXRbeta enhances the affinity of LXR towards SRC-1 and thereby brings $Eu^{3+}$ and APC in close proximity. $Eu^{3+}$ is excited at 337 nm and emitts light at 620 nm. This emission, when in close proximity, excites APC to emit light at 665 nm.

Dilution plates with compounds in DMSO were further diluted in buffer {20 mM [Tris(hydroxymethyl)aminomethane] pH 7.5, 0.125% CHAPS {3-[(3-Cholamidopropyl)dimethylammonio]-1-propanesulfonate}, 2 mM DTT (Dithiothreitol) and 0.05% BSA (Bovine Serum Albumin)} in order to reduce DMSO concentration, 0.5 µl to 13.5 µl. To this, 6 µl assay mix was added and the plates (384-well V-groove plates) were incubated at room temperature for 60 to 80 min. The assay mix has the following final concentrations; LXRalpha mix: 0.06 µg/mL Eu-labelled anti-6x His Ab, 1.15 µg/mL Streptavidin APC, 30 nM SRC-1 peptide and 0.9 µg/mL LXRalpha in buffer and LXRbeta mix; 0.06 µg/mL Eu-labelled anti-6x His Ab, 1.15 µg/mL Streptavidin APC, 90 nM SRC-1 peptide and 0.2 µg/mL LXRbeta in buffer. Time-resolved fluorescence readings were done in a Wallac Victor reader at 665 nm followed by reading at 615 nm. The LXR ligand, 22-R Hydroxycholesterol at 50 µM was used as the 100% control.

Transactivation Assay

Expression vectors were prepared by inserting the ligand binding domain cDNA (complementary DNA) of human LXRalpha (amino acid 205-447) and LXRbeta (amino acid 216-461) in frame with, 3' to the yeast GAL4 transcription factor DNA binding domain and the nuclear localization signal from the T-antigen of Polyoma Virus in the eucaryotic expression vector pSG5 (Stratagene). The resulting expression vectors pSGGAL-LXRalpha and pSGGAL-LXRbeta were used in cotransfection experiments together with the pGL3 luciferase reporter plasmid containing a minimal SV40 promoter and five copies of the UAS GAL4 recognition site. 2.5 µg pSGGAL-LXRalpha or beta were mixed with 25 µg pGL3 5xUAS and 22.5 µg pBluscript in 0.95 mL ice cold PBS containing approx. 4-9 milj. U2/OS osteosarcoma cells. After a five minute incubation on ice the cell/DNA mixture was electroporated in 0.4 cm cuvettes at 960 µF, 230 V using a BioRad electroporator and diluted to 0.32 milj cells/mL in complete DMEM (Dulbecco's Modified Eagle Medium) medium (Gibco 31966-021). Cells from at least two electroporations were pooled in order to avoid variations between different electroportations. 25 µl diluted, electroporated cells, were seeded onto 384-well plates (0.8×10⁴ cells/well) and the cells were allowed to adhere for 2 h at 37° C., 5% $CO_2$ in a cell culture incubator. Dilution plates with compounds in DMSO were further diluted in DMEM w/o phenol red (Gibco 11880-028) including 10% FBS (Foetal Bovine Serum), 1% PEST (Penicillin Streptomycin), 20 mM Hepes, 2 mM L-Glutamine and 0.36% Glucose (2.5 µto 97.5 µl) in order to reduce DMSO concentration. 7 µl of this was added to the electroporated cells in 384-well plates and incubation was continued for 48 h in a cell culture incubator, after which cells were lysed by adding 32 µl/well LucLite luciferase substrate. Luciferase activity was measured using the "Luminescence 384 protocol" in the Wallac Victor reader after 15 min. incubation at room temperature. The LXR ligand, Tularik T0901317, at 1 µM was used as the 100% control.

The compounds of formula I have an $EC_{50}$ of less than 50 µmol/l for LXRalpha and/or beta in coactivator recruitment assays and/or reporter gene assays. For example, the compounds of Examples 13 and 22 were $EC_{50}$'s of 0.15 µmol/l and 0.11 µmol/l in coactivator recruitment assays, respectively.

In addition the compounds of the present invention exhibit improved physical and/or chemical and/or DMPK (Drug Metabolism and Pharmacokinetic) properties, for example they exhibit improved metabolic stability in vitro, and/or exhibit favourable pharmacological effects in vivo. The compounds also have a promising toxicological profile.

The invention claimed is:
1. A compound of Formula I:

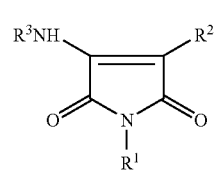

Formula I or a pharmaceutically acceptable salt thereof,
wherein
$R^1$ is pyridyl(1-4C)alkyl wherein the pyridyl is optionally substituted by (1-4C)alkyl or a group of formula $NR^aR^b$ in which $R^a$ and $R^b$ independently represent H or (1-4C)alkyl;
$R^2$ is phenyl; and
$R^3$ is selected from phenyl optionally substituted by one or more of the following: (1-3C)alkanoyl; (1-3C)alkoxy optionally substituted by one or more fluoro; (1-3C)alkylthio; or a group of formula $NR^aR^b$ in which $R^a$ and $R^b$ independently represent H, (1-3C)alkyl or (1-3C)alkanoyl.

2. A compound according to claim 1 in which $R^1$ is selected from 2-pyridylmethyl, 3-pyridylmethyl, 4-pyridylmethyl or 6-amino-3-pyridylmethyl.

3. A compound according to claim 1 or claim 2 in which $R^3$ is selected from phenyl, 4-methoxyphenyl, 4-methylthiophenyl, 4-acetylaminophenyl, 4-trifluoromethoxyphenyl or 4-difluoromethoxyphenyl.

4. A compound according to claim 1 in which
$R^1$ is selected from 2-pyridylmethyl, 3-pyridylmethyl, 4-pyridylmethyl or 6-amino-3-pyridylmethyl;
$R^2$ is phenyl; and
$R^3$ is selected from phenyl, 4-methoxyphenyl, 4-acetylaminophenyl or 4-difluoromethoxyphenyl.

5. A compound according to claim 1 in which
$R^1$ is selected from 6-amino-3-pyridylmethyl or 3-pyridylmethyl;
$R^2$ is phenyl; and
$R^3$ is selected from 4-methoxyphenyl, 4-difluoromethoxyphenyl or 4-trifluoromethoxyphenyl.

6. A compound according to claim 1 in which
$R^1$ is selected from 6-amino-3-pyridylmethyl or 3-pyridylmethyl;
$R^2$ is phenyl; and
$R^3$ is selected from 4-methoxyphenyl or 4-difluoromethoxyphenyl.

7. A compound according to claim 1 in which
$R^1$ is selected from 6-amino-3-pyridylmethyl;
$R^2$ is phenyl; and
$R^3$ is selected from 4-trifluoromethoxyphenyl or 4-difluoromethoxyphenyl.

8. A compound according to claim 1 in which
$R^1$ is selected from 6-amino-3-pyridylmethyl or 3-pyridylmethyl;
$R^2$ is phenyl;
$R^3$ is selected from 4-trifluoromethoxyphenyl or 4-difluoromethoxyphenyl.

9. A compound selected from the following:
3-Phenyl-1-(pyridin-3-ylmethyl)-4-{[4-(trifluoromethoxy)phenyl]amino}-1H-pyrrole-2,5-dione;
3-[(4-Methoxyphenyl)amino]-4-phenyl-1-(pyridin-3-ylmethyl)-1H-pyrrole-2,5-dione;
3-Anilino-4-phenyl-1-(pyridin-3-ylmethyl)-1H-pyrrole-2,5-dione;
3-[[4-(Difluoromethoxy)phenyl]amino]-4-phenyl-1-(pyridin-3-ylmethyl)-1H-pyrrole-2,5-dione;
3-[(4-Methoxyphenyl)amino]-4-phenyl-1-(pyridin-4-ylmethyl)-1H-pyrrole-2,5-dione;
3-[(4-Methoxyphenyl)amino]-4-phenyl-1-(pyridin-2-ylmethyl)-1H-pyrrole-2,5-dione;
1-[(6-Aminopyridin-3-yl)methyl]-3-[(4-methoxyphenyl)amino]-4-phenyl-1H-pyrrole-2,5-dione; and
1-[(6-Aminopyridin-3-yl)methyl]-3-{[4-(difluoromethoxy)phenyl]amino}-4-phenyl-1H-pyrrole-2,5-dione;
or a pharmaceutically acceptable salt thereof.

10. A process for the preparation of a compound according to claim 1, comprising reacting a compound of formula II,

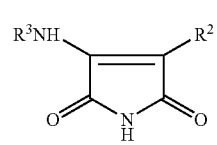

(II)

wherein $R_2$ and $R_3$ are as defined in claim 1, with a compound of formula III,

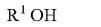

(III)

wherein $R_1$ is as defined in claim 1, in the presence of dialkyl azodicarboxylate and a phosphine, optionally in the presence of an inert organic liquid at a temperature in the range of 0° C. to 200° C.

11. A process for the preparation of a compound according to claim 1, comprising reacting a compound of formula IV,

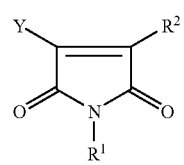

(IV)

wherein $R^1$ and $R^2$ are as defined in claim 1 and Y is Cl, Br or I, with a compound of formula V,

(V)

wherein $R^3$ is as defined in claim 1, optionally in the presence of an inert organic liquid, and optionally in the presence of a base, at a temperature in the range of 0° C. to 250° C.

12. A pharmaceutical formulation comprising a compound according to claim 1 in admixture with a pharmaceutically acceptable adjuvant, diluent or carrier.

* * * * *